United States Patent
Walker et al.

(10) Patent No.: US 10,045,655 B2
(45) Date of Patent: Aug. 14, 2018

(54) LIQUID-ACTIVATED LIGHT AND INFUSING APPARATUS

(71) Applicant: Vibe, LLC, Starkville, MS (US)

(72) Inventors: Hagan D. Walker, Columbus, MS (US); Kaylie L. Mitchell, Starkville, MS (US)

(73) Assignee: Vibe, LLC, Starkville, MS (US)

( * ) Notice: Subject to any disclaimer, the term of this patent is extended or adjusted under 35 U.S.C. 154(b) by 22 days.

(21) Appl. No.: 15/164,354

(22) Filed: May 25, 2016

(65) Prior Publication Data

US 2017/0009972 A1    Jan. 12, 2017

Related U.S. Application Data

(60) Provisional application No. 62/191,502, filed on Jul. 12, 2015.

(51) Int. Cl.
| | |
|---|---|
| *F21V 23/00* | (2015.01) |
| *A47J 31/44* | (2006.01) |
| *A61K 9/00* | (2006.01) |
| *A61J 7/00* | (2006.01) |
| *F21V 33/00* | (2006.01) |
| *F21V 23/04* | (2006.01) |
| *A47J 31/40* | (2006.01) |
| *F21W 121/00* | (2006.01) |

(52) U.S. Cl.
CPC ......... *A47J 31/4403* (2013.01); *A47J 31/401* (2013.01); *A47J 31/407* (2013.01); *A47J 31/44* (2013.01); *A61J 7/00* (2013.01); *A61K 9/00* (2013.01); *F21V 23/04* (2013.01); *F21V 33/0036* (2013.01); *F21W 2121/00* (2013.01)

(58) Field of Classification Search
CPC ...... A47J 31/4403; A47J 31/401; A47J 31/44; A61J 7/00; A61K 9/00; F21V 23/04; F21V 33/0036; F21W 2121/00
USPC ................................................. 362/190, 158
See application file for complete search history.

(56) References Cited

U.S. PATENT DOCUMENTS

| | | |
|---|---|---|
| 3,818,208 A | 6/1974 | Kahl |
| 6,007,853 A | 12/1999 | Lesser |
| 6,168,816 B1 | 1/2001 | Hammond |
| 6,669,352 B2 | 8/2003 | McKinney |
| 6,966,666 B2 | 11/2005 | Liu |
| 7,049,766 B2 | 5/2006 | Lewis |
| 8,205,542 B2 | 6/2012 | Gilbert |
| 2003/0090897 A1 | 5/2003 | Su |
| 2008/0273319 A1 | 7/2008 | VanderSchuit |
| 2009/0141484 A1 | 6/2009 | Torres |
| 2010/0209560 A1 | 8/2010 | Demarse |
| 2014/0043799 A1* | 2/2014 | Dayan ................... F21V 31/005 362/158 |

* cited by examiner

*Primary Examiner* — Karl D Frech
(74) *Attorney, Agent, or Firm* — Michael C. Williams; Bradley Arant Boult Cummings LLP

(57) ABSTRACT

The present invention provides a novel method and apparatus for a liquid-activated, lighted and flavored drink infuser. The invention enhances the beverage and drink experience for any user by providing a liquid-activated, lighted, flavored drink infuser that, when placed in liquid, will light up and/or release into the liquid specific contents inside the infuser, such as flavoring(s) and/or medicine(s).

17 Claims, 6 Drawing Sheets

LIQUID-ACTIVATED LIGHT AND INFUSING APPARATUS

CROSS-REFERENCE TO RELATED APPLICATIONS

This application claims priority to and the benefit of U.S. Provisional Application No. 62/191,502, filed 12 Jul. 2015 titled "Liquid-Activated Drink Infuser". All of the foregoing application(s) are incorporated herein by reference in their entireties.

BACKGROUND

A. Field of the Disclosure

This present disclosure relates generally to an enclosed liquid-activated light for drink illumination, decoration and flavor infusion.

B. Background

Lighted items have long been placed in liquid beverages to add an element of excitement to an event. However, typically this is accomplished by use of two lighted devices that is either: (a) a glow-stick; or (b) an apparatus or device that is lit prior to placing said device into the liquid, requiring user interaction.

The device, hereinafter known as Liquid-activated light and infusing apparatus, provides the excitement previously provided by lighted items in beverages, or any liquid-filled container, but with two unique features: internal liquid-activation and flavor infusion.

SUMMARY

The applications described above are accomplished by the device described in this disclosure, although it is to be understood that not all such applications will be accomplished by every embodiment of the device.

The device is a safe and decorative device that can be placed in a liquid, most commonly a consumable and, translucent beverage, and illuminates upon submersion in said liquid, comprising: a shell, a base, and a printed circuit board (PCB); the shell having a plurality of openings placed strategically to aid in the sinking of the device by allowing air to escape from the device; the base having a lower section with a plurality of openings strategically placed to aid in the sinking of the device by letting said liquid enter the device, an upper section with a cavity to house the PCB, and a cover enclosing the PCB within the base with a plurality of openings exposing the tip of the plurality of the conductive probes located on the PCB; the PCB having a power source, a light-emitting diode (LED), at least one conductive probe, and a minimum of one transistor circuit; wherein the presence of a liquid acts as a switch by creating a bridge that closes the circuit, and in turn, illuminates the device; and wherein the removal of the liquid immediately, or over a short period of time, opens the circuit, discontinuing the illumination.

Additionally, the device may be fitted with a soluble substance within the shell of the liquid-activated light and infusing apparatus which is dispersed throughout the liquid upon insertion by use of the strategically placed openings located on the shell and lower section of the base.

DETAILED DESCRIPTION

A. Definitions

Figure 1:
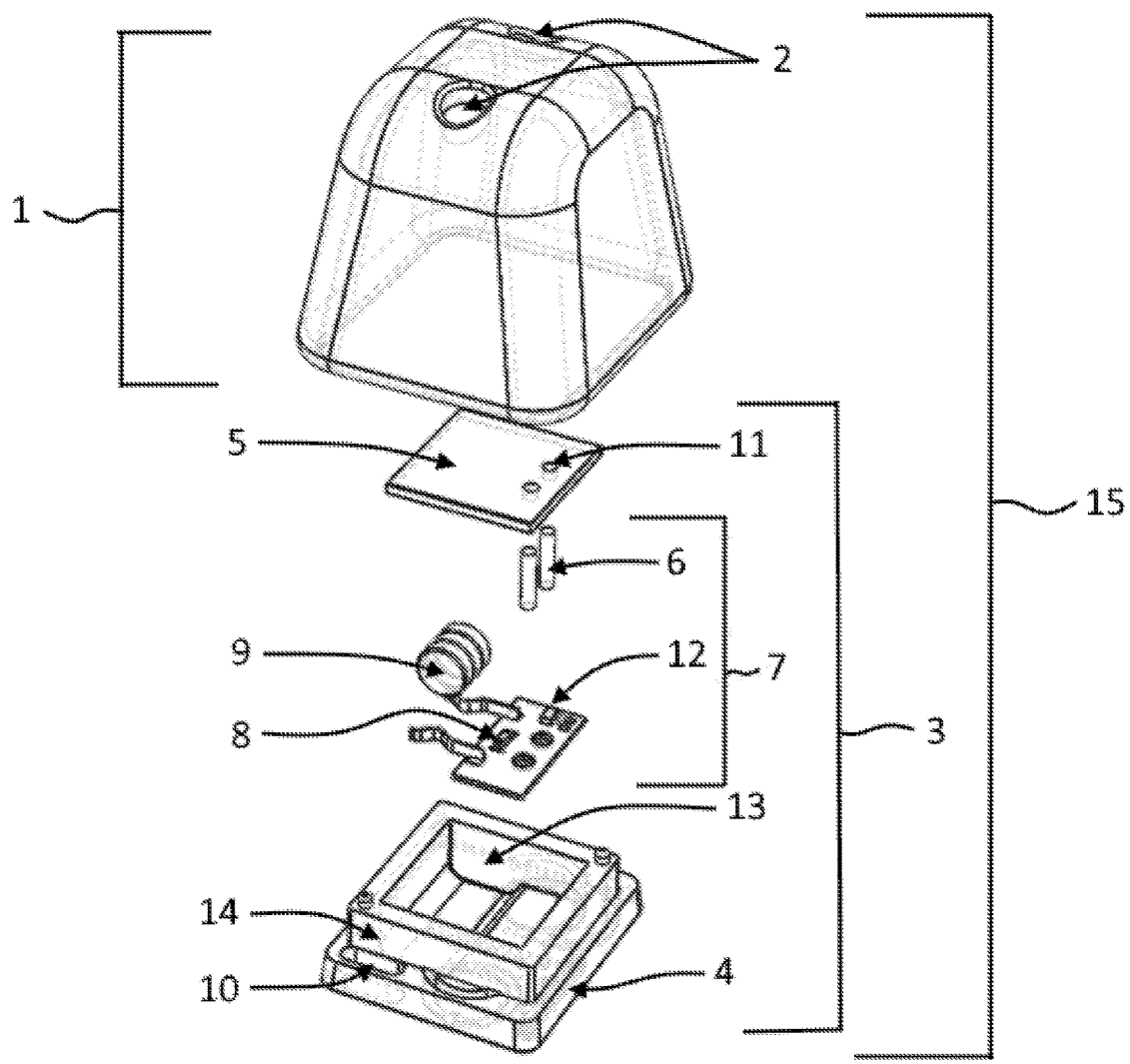
FIG. 1 shows an isometric view of the entire unit, showing a generic shell.
Figure 2:
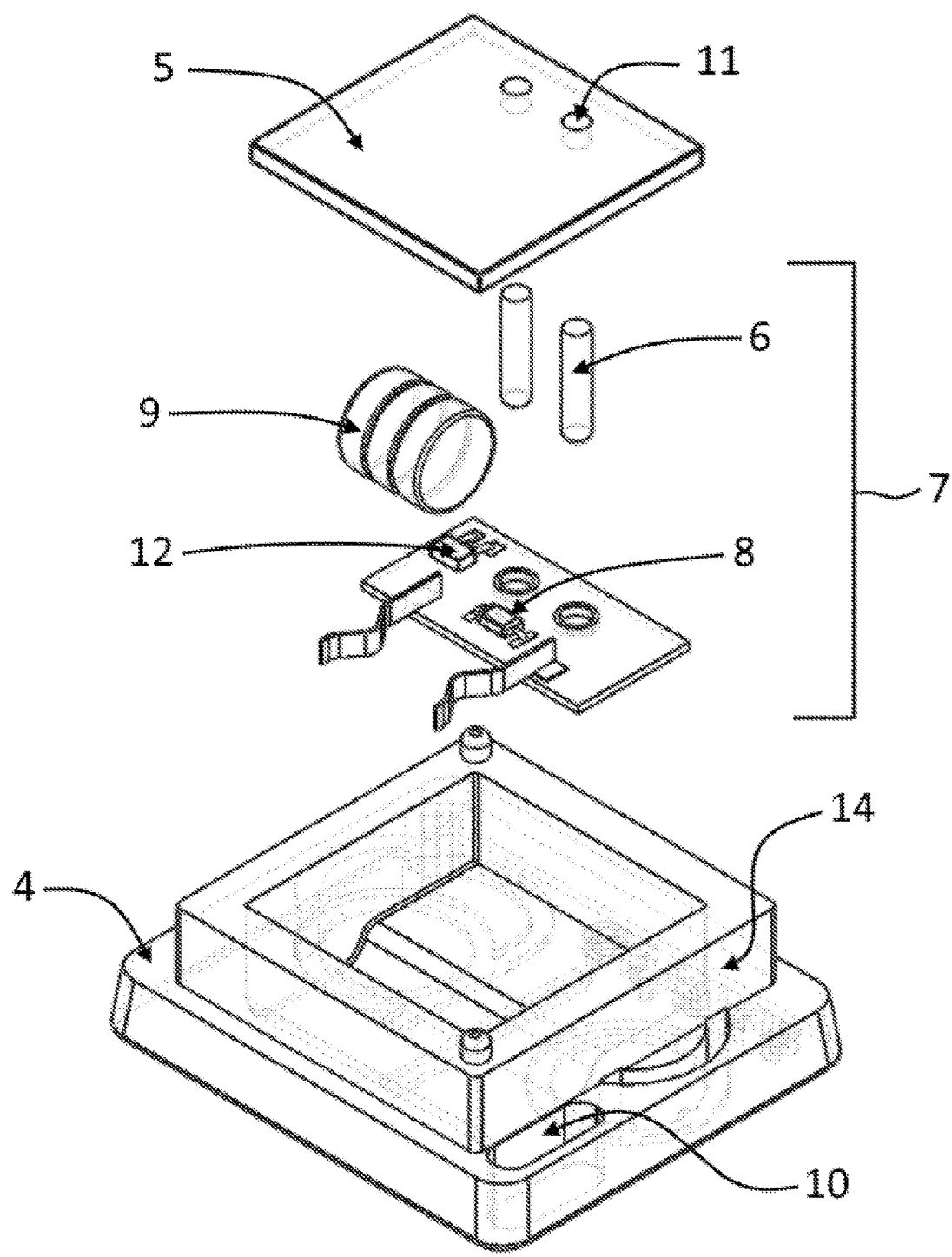
FIG. 2 shows an enlarged isometric view of the base of FIG. 1.
Figure 3:
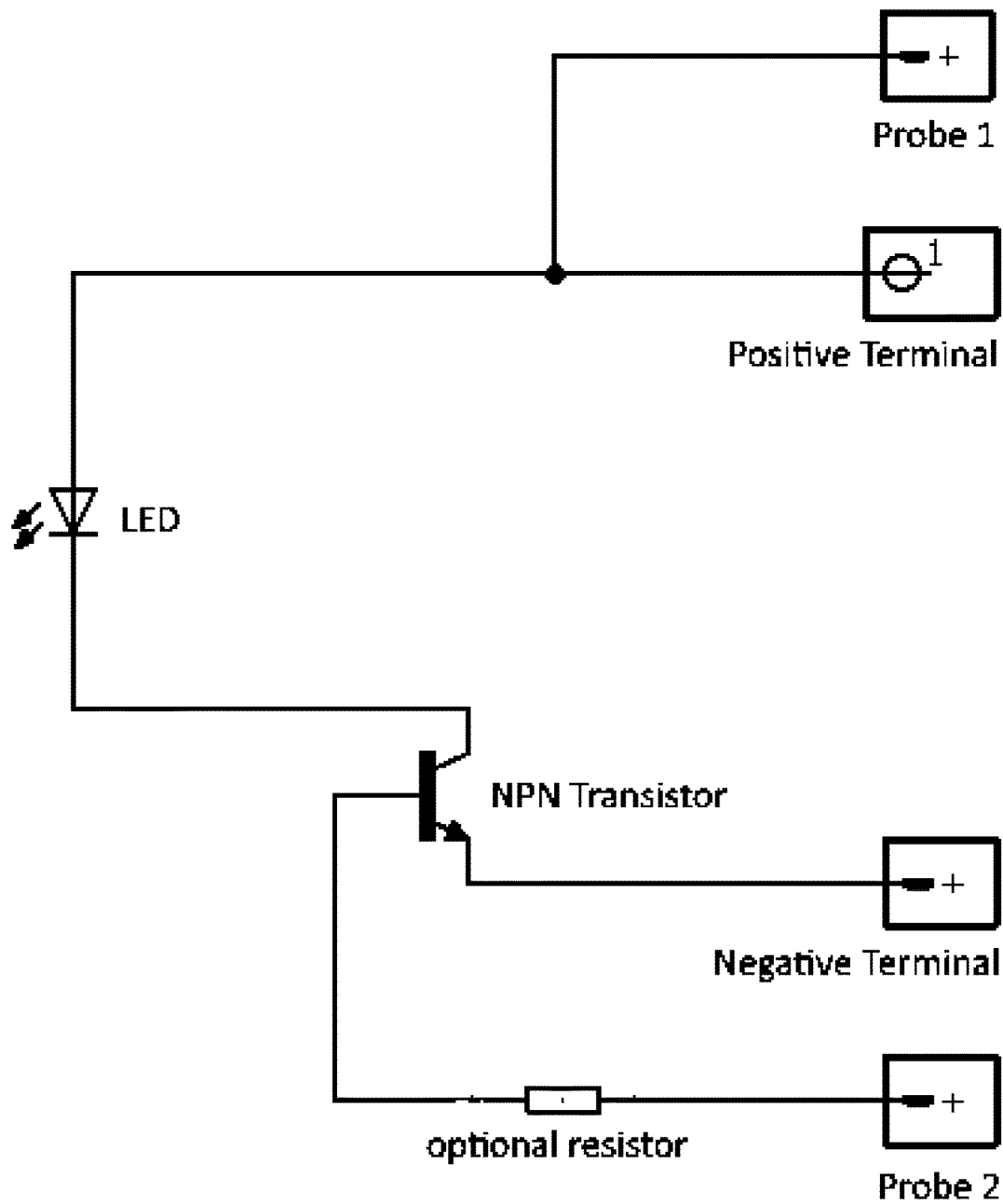
FIG. 3 shows an electrical schematic of the circuit used in the device.
Figure 4:
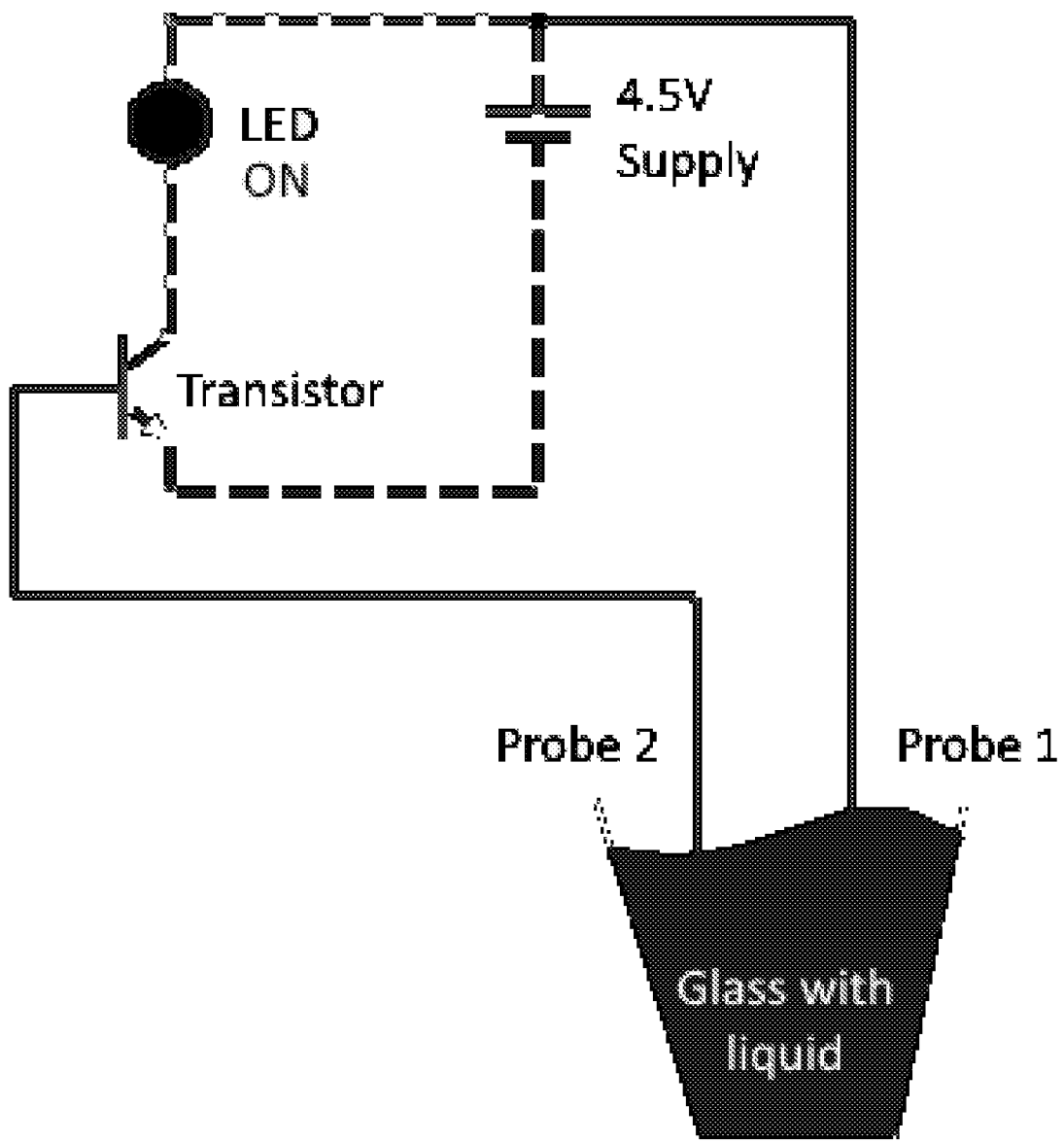
FIG. 4 shows an electrical simulation of the circuit when inserted into a liquid.
Figure 5:
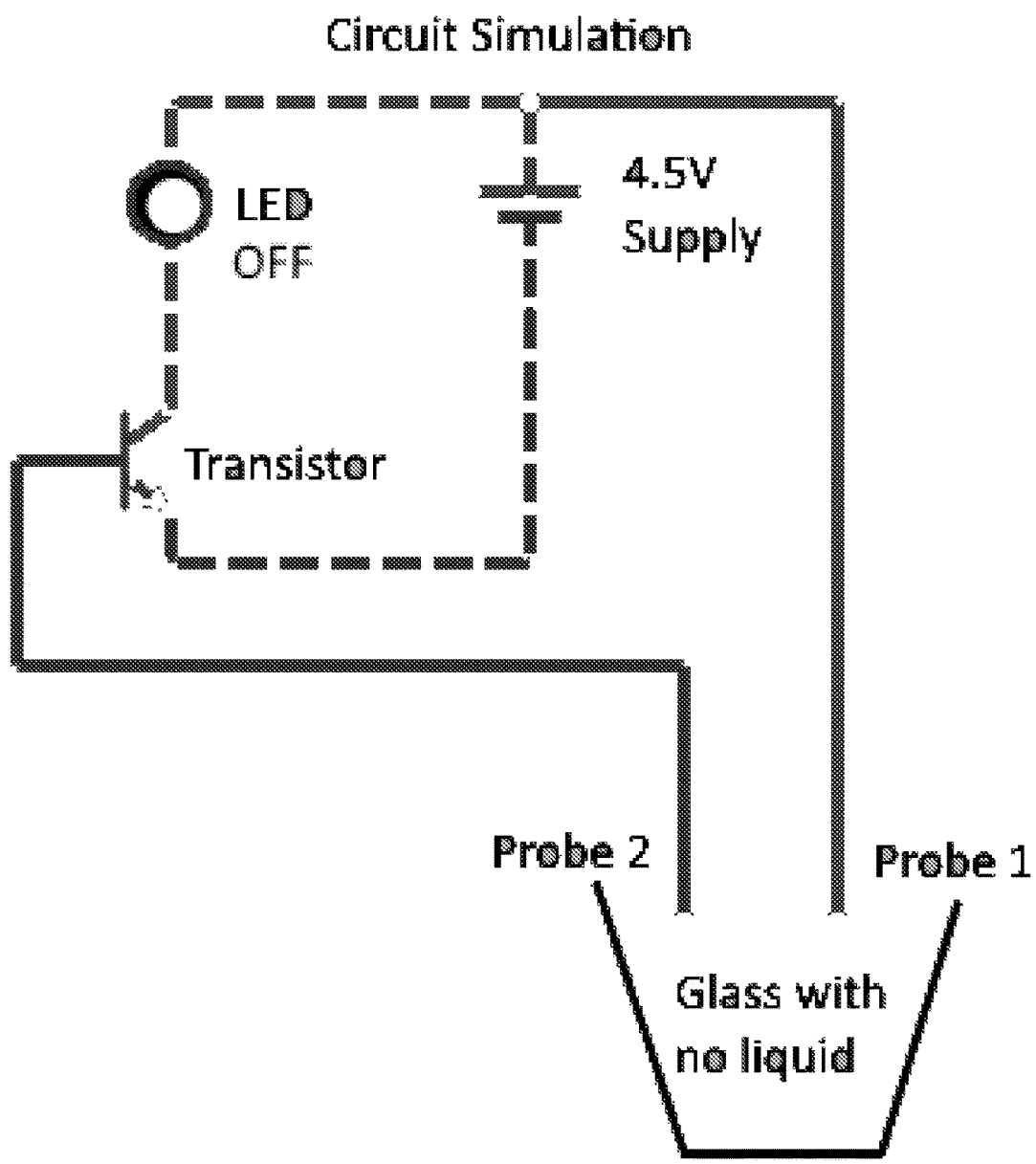
FIG. 5 shows an electrical simulation of the circuit when no liquid is present.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another when the apparatus is right side up.

With reference to the use of the words "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and the following claims.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

B. Liquid-Activated Light and Infusing Apparatus

The liquid-activated light and infusing apparatus is a device when placed in a liquid, illuminates, filling the container holding the liquid with a display of light and excitement, as long as the liquid is present. The liquid activated light and infusing apparatus can also be fitted with a soluble substance in the shell of the device that allows for the dispersion or infusion of the substance throughout the liquid.

This liquid activation feature is important as the absence of liquid can serve as a prompt to act, subject to the device's use, since the illumination of the unit will discontinue without said liquid. For example, when in a bar or restaurant environment, the liquid-activated light and infusing apparatus allows a bartender or waiter to quickly determine when a user's drink is empty.

The disclosed device is a device that illuminates when placed into a liquid. In addition the device also has the ability to release contents located inside the internal infuser. Subsequent to the liquid being consumed or removed, the lighting apparatus turns off and the diffuser dries so that the light is no longer emitted. Similarly, once removed from the liquid, the flavoring is no longer released, and remains in the shell. The colors that are displayed by the device can be any color or combination. Further, the flavoring, or any soluble substance, can be any palatable flavoring and/or medicine(s) to be taken or consumed by the user.

1. First Embodiment

The first embodiment of the invention is a safe and decorative device 15 that can be placed in a liquid, most commonly a consumable, translucent beverage, that illuminates upon submersion in said liquid, comprising: a shell 1, a base 3, and a printed circuit board (PCB) 7. The shell 1 has, in one embodiment, a plurality of openings 2 placed strategically to aid in the submersion of the device 15 in the liquid. The base 3 having a lower section 4 with a plurality of openings 10 strategically placed to aid in the sinking of the device 15, an upper section 14 with a cavity 13 to house the PCB 7, and a cover 5 enclosing the PCB 7 within the cavity 13 of the upper section 14 of base 3 with plurality openings 11 exposing the surface of the plurality of the conductive probes 6 located on the PCB 7. The PCB 7 having a power source 9, a light-emitting diode (LED) 8, at least one conductive probe 6, and a minimum of one transistor circuit 12; wherein the presence of a liquid acts as a switch by creating a bridge that closes the circuit and in turn illuminates the device 15; and wherein the removal of the liquid immediately, or over a short period of time, deactivates the circuit, discontinuing the illumination.

The shell 1 is outer layer of the device 15. The shell 1 is not limited to any specific shape or size, but is customizable to take the shape for any purpose as the user sees fit. The shell 1 houses the base 3 in the shape or design desired by the user. The shell 1 contains a plurality of holes 2 to allow the entry of the liquid to activate the electrical circuit on the PCB 7, by liquid contacting the surface of the conductive probes 9, and also ensuring that the device 15 fills with the liquid that it is placed within. Moreover, the shell 1 is made of a food grade plastic, including but not limited to, polystyrene or polypropylene that at a minimum is translucent, and preferably transparent.

Similar to the shell 1, the base 3 is not limited to any specific shape or size, but is customizable, subject to the shape and size of the shell 1 i.e., the shell 1 and base 3 must be able to fit together. The only requirement is that the base 3 is large enough to house the PCB 7 within the cavity 13 of the upper section 14, exposing only the surface conductive probes 6 to the interior of the shell 1. The base 3 consists of three components, the lower section 4, upper section 14, and the cover 5. The lower section 4 contains a plurality of openings 10, which in conjunction with the openings 2 located on the shell 1, allow the liquid to enter the shell 1, active the electrical circuit on the PCB 7, and ensure the device 15 sinks. The plurality of openings 10 on the base 3 are placed so as to allow the entry of the liquid into the shell 1 and not the cavity 13 of the base 3 where the PCB 7 is housed. The upper section 14 contains a cavity 13 for the placement of the PCB 7 and the cover 5 is affixed to the upper section 14 via hermetic seal, preventing the entry of said liquid, corrosion of the PCB 7 and possible contamination from said liquid. The cover 5 also includes a plurality of openings 11, identical in number to the number of conductive probes 6 contained on the PCB 7, sealed and exposing only the surface of the conductive probes 6 to allow for the activation of the electrical circuit of the PCB 7 and illuminate the LED 8. The entire base 3, similar to the shell 1, is made of a food grade plastic that at a minimum is translucent, and preferably transparent.

Finally, the PCB 7 is placed and configured within the cavity 13 of the upper section 14 and covered and sealed by the cover 5 so that the surface of the plurality of conductive probes 6 are exposed to the liquid for activation and closing of the circuit.

The PCB 7 consists of a power source 9, at least one LED 8, at least one conductive probe 6, and a minimum of one transistor 12. The arrangement of the PCB 7 is capable of multiple configurations based on the shape of the device 15 itself. The power source 9, creates the initial flow of electricity for the current to power the light. Most often, this power source 9 is a series of coin cell batteries, providing a nominal supply of 4.5 volts.

The PCB assembly 7 unit comprises of electronics that are sealed for safety to protect the user and all conductive probes 6 are composed of corrosion-proof, conductive materials which may include, but are not limited to stainless steel or other corrosion proof metals. The LED 8 may operate in a variety of modes, for example: it may alternate colors; it may remain one single color; it may flicker or project a continuous stream of light; and the color and intensity may be controlled by a third party.

In one embodiment, the plurality of conductive probes 6 are configured as such: a first probe is connected to the positive voltage of the power source 9; and a second probe is connected to the base of the transistor 12. When the two probes 6 are connected, such as when placed in a liquid, electrons are allowed to flow proportionally between the collector and emitter, completing said circuit.

The transistor 12 is of negative-positive-negative (NPN) variety, placed in between the LED's 8 cathode and circuit's ground. When the transistor 12 has a positive voltage on the base, the transistor 12 allows electrons to flow proportionally to the base voltage between the collector and emitter, closing the circuit. When there is no positive voltage being applied to the base, electrons are not allowed to flow between the collector and emitter, essentially opening the circuit.

The method and system of the invention uses the naturally-conductive characteristic of ions in water and liquid, for example, to utilize such liquid as a switch. The invention provides at least two metal or electrically-conductive probes 6 that are not exposed to the outside of the shell 1. Instead, the liquid enters the interior of the shell 1 itself, where the conductive probes 6 are located from the cover 5 of the base 3, as previously mentioned. Once the conductive probes 6 contact the liquid, the liquid acts as a switch between said probes 6, thereby allowing current from the power source to flow through the transistor 12 inside the sealed unit, completing the circuit and providing power to the LED 8 for illumination. A reverse of this conductive process occurs when the device 15 is removed from the liquid, wherein the liquid bridge is removed and the connection between probes 6 is also removed opening the circuit and, deactivating the device 15.

The device 15 is designed to sink once inserted into the liquid, so as to prevent ingestion of the device 15 by the user, but can also float or remain suspended in said liquid. Sinking is accomplished through the design of the invention which allows the liquid to travel through openings and as a result, increases the object's density, and therefore, forces the object to the bottom of the container, to ensure that water enters the shell 1 unit the device 15 sinks. The device 15 will remain at the bottom of the liquid container to protect the user/drinker and will not interfere with user's action of drinking or bump the user's mouth as the liquid is consumed. However, the device can be made to float by changing the density of the base 3.

The device, most commonly, is a single use device 15; however, the device 15 can be reused in most applications without alteration, and with proper sterilization, in the medical context. Further, the shell 1 for the disclosed invention can take on a number of shapes and sizes depending on the event or occasion, including but not limited to, sport's and company logos.

2. Second Embodiment

Further, the invention provides an embodiment that contains a dispersion methodology and system to provide for the release of specific contents, such as flavoring(s), medicine(s), or any soluble substance, from the device 15 and into the liquid, in a predetermined amount and rate. This embodiment is comprised of the same components: a shell 1, a base 3, and an printed circuit board (PCB) 7; the shell 1 having a plurality of openings 2 placed strategically to aid in the sinking of the device 15; the base 1 having a lower section 4 with a plurality of openings 10 strategically placed to aid in the sinking of the device 15, a cavity 13 within the lower section 4 of the base 3 to house the PCB 7, and a cover 5 enclosing the PCB 7 within the base 3 with two openings 11 exposing the tip of the plurality of the conductive probes 9 located on the PCB 7; the PCB 7 having a power source 9, an LED 8, at least one conductive probe 6, and a minimum of one transistor circuit 12; wherein the presence of a liquid acts as a switch by creating a bridge that completes the circuit and in turn illuminates the device 15; and wherein the removal of the liquid immediately, or over a short period of time, deactivates the circuit, discontinuing the illumination. However, this particular embodiment is unique in that the user may place a number of items in the shell 1, including but not limited to, any flavoring(s), medicine(s) or soluble substance appropriate for the user's application.

In this embodiment, the openings 2 located in the shell 1 and lower section 4 of the base 3 serve an additional purpose; to allow for, and facilitate, the equal and systematic dispersion of the soluble substance whether that is flavoring, medicine or any soluble substance throughout the liquid.

The substance is contained in each device, which has a plurality of openings of predetermined size that allows water or liquid to enter the shell 1 and the substance, typically pressed powder, to exit or escape and mix with the water or liquid, without interrupting or interfering with the lighting mechanism of the device 15. This is accomplished in conjunction with the sinking process. During this process, which begins once the device 15 is placed in the liquid, liquid quickly enters the shell 1 of the device 15 while air rapidly escapes from the shell 1. The soluble substance immediately begins to dissolve into the liquid as the device 15 continues sinking to the bottom of the container, simultaneously dispersing the dissolved particles throughout the liquid. Medicinal uses of the present invention include diffusion of medications placed in the unit to be administered to a patient or individual in need thereof via a water carrier or other liquid carrier.

3. Third Embodiment

Figure 6:
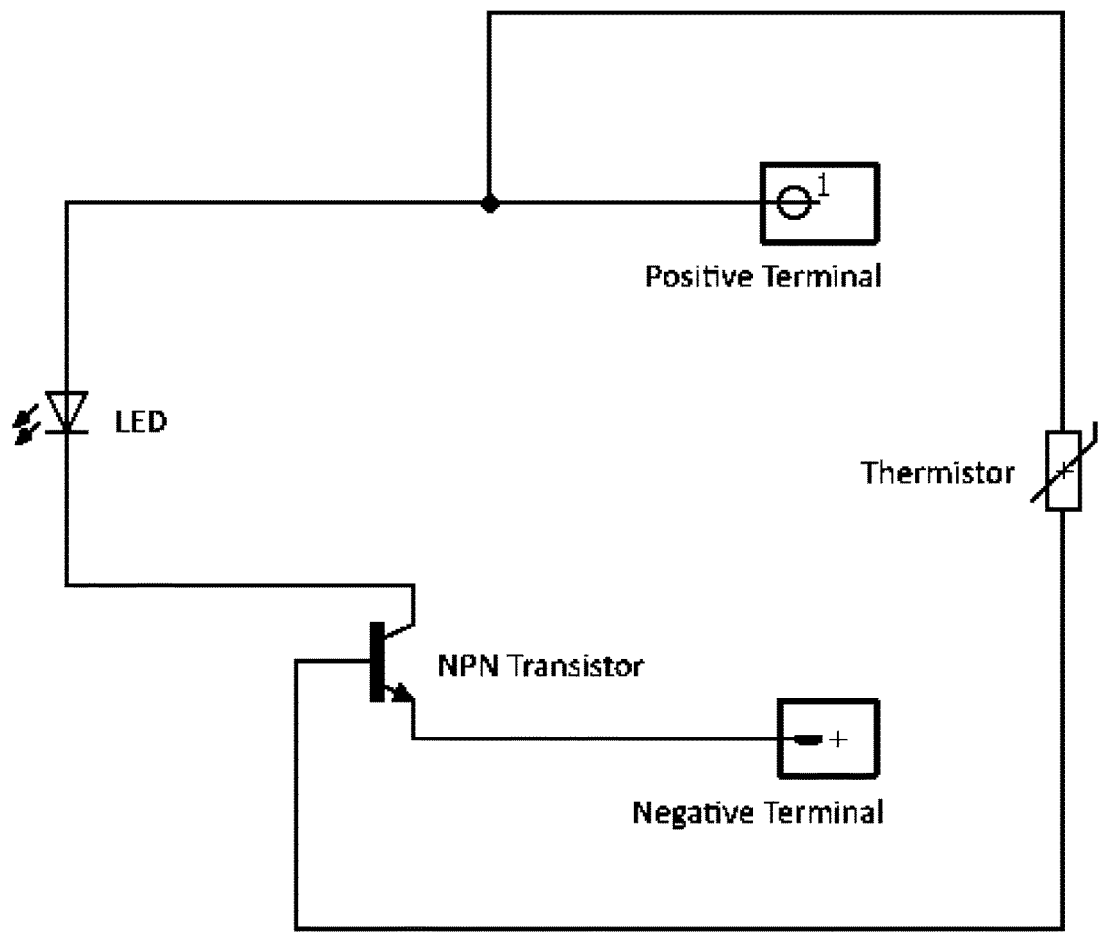
FIG. 6 shows an electrical schematic of the circuit when a thermistor is used in place of the probes.

This embodiment is comprised of the similar components: a shell 1, a base 3, and an printed circuit board (PCB) 7; the shell 1 having a plurality of openings 2 placed strategically to aid in the sinking of the device 15; the base 1 having a lower section 4 with a plurality of openings 10 strategically placed to aid in the sinking of the device 15, a cavity 13 within the lower section 4 of the base 3 to house the PCB 7, and a cover 5 enclosing the PCB 7 within the base 3 with no openings 11. A thermistor would be used instead of conductive probes as illustrated in FIG. 6, located on the PCB 7; the PCB 7 having a power source 9, an LED 8, a thermistor, and a minimum of one transistor circuit 12; wherein temperature fluctuations change the brightness, intensity, or color of the LED. The majority of the components operate in the same fashion as disclosed in the previous embodiments however, the addition of the thermistor allows exterior temperatures to regulate the brightness, intensity, or color of the LED 8.

4. Additional Embodiments

In addition to submerging the entire unit in a consumable liquid, the device 15 can be assembled in the form of a straw, wherein the base 3 is affixed to the straw so that the passing liquid activates the LED 8 once the user takes a sip of his or her drink.

Unlike the prior art, the printed circuit board, components, and conductive probes bare housed inside of the base unit, which in turn is housed inside of the shell unit, as described above. This distinguishes the device from the prior art in that it prevents "false reads" when the device is more or less empty because the conductive probes 6 are located inside of the shell 1. A false read occurs when the user's beverage, for all intents and purposes is empty, however, should the drink contain ice or residual liquid, and contact with the ice and/or residual liquid may trigger the conductive probes if they were located on the exterior of the device, and as a result, illuminate the device. This is problematic as one of the features of the liquid-activated light and infusing apparatus is to potentially alert bartenders, or waiters, of an empty drink, which is completely defeated by "false reads". The encasing of the base 3 in the shell 1 with the conductive probes 6 protruding from the top of the base 3 prevents "false reads," and therefore, adds additional, and more efficient, applications.

In addition, the prior art completely lacks the ability to house additional components such as flavoring(s), medicine(s), or any soluble substance. This is important as this feature enlarges the scope of the liquid-activated light and infusing apparatus's application. The addition application(s) allows a medical facility to place the requisite medicine, preferably in the form of a pressed dissolvable tablet, into the shell of the liquid-activated light and infusing apparatus. Once inserted into a drink, the substance is quickly dispersed throughout the liquid. The illumination of the glass distracts the patient and promotes a fun, enjoyable experience for the patient, particularly when the patient is a young child. This application is not limited to the medical field as the shell may be filled with any soluble substance that the user sees fit, such as use in a clear vase filled with nutrients for the flowers, or an aquarium, filling Liquid-activated light and infusing apparatus with food.

Finally, the prior art fails to disclose a device that sinks upon insertion into a liquid, and in fact teaches devices that, by design, float. Liquid-activated light and infusing apparatus is designed to sink for the following reasons: it serves as a safety mechanism to prevent accidental ingestion; it propels the dispersion of the soluble substance contained in the shell, a feature that would lose efficiency should it remain at the top of the beverage; and it ensures that the device is fully submerged at all times, limiting the possibility of a failed switch.

The device is beneficial to multiple users in a variety of settings, including, but not limited to, personal uses and more commonly, commercial uses such as social bars, clubs, restaurants, hospitals, medical facilities, organized social gatherings, and the like. Further, the use of the invention is not limited to use in a consumable liquid, but may also be used as a décor in items such as vases or the like. The device is customizable by shape, size, soluble substance, and light color. The customization features allow users to have the unit built for a specific atmosphere or event. It also allows medical treatment in a unique way, one that makes taking medicine fun, enjoyable, and interesting for people and animals of all ages or for any subject in need thereof. Food and drink servers can easily see when a drink is low or empty and can provide more timely service to the customer. The device can have many different shapes and sizes, both functional and non-functional, and provides a sanitary and safe alternative to or replacement for real fruit, or decorations that typically must be cut and added to certain drinks in addition to having a limited shelf life. Medical providers can easily and at a glance observe when a patient has completed medication. The device is safe to keep by users as a toy or memento. It can also be made to be reusable, based on the flavoring life and light source life. The invention provides an enhanced experience to everyday liquids, whether it be solely for consumption or décor, on a personal level at home, or in a public setting.

C. Prophetic Example

The preferred embodiment of the disclosed device is comprised of three components, a shell, base and PCB, that combine to form a safe and decorative device that illuminates when be placed in a liquid, and ceases illumination once removed from said liquid. The completed device is assembled in a fashion where the PCB is inserted into a cavity contained in the upper section of the base and the base is inserted into the shell, creating an enclosed, semi-hollow apparatus for placement in a liquid. The shell and base are made of a transparent, food grade plastic. As the intake of the liquid through the openings located on the top of the shell increases the object's density, and therefore, forces the object to the bottom of the container; Once the device is inserted into a liquid, the liquid enters an opening contained on the shell unit and makes contact with the exposed surface of the probes of the PCB. The liquid creates a switch, completing the circuit and illuminating the LED on the PCB. Once the apparatus is removed from the liquid, the switch is deactivated and the device ceases illumination.

The shell is a device made of a transparent, food grade plastic in the shape of a hollow, truncated rectangular pyramid with an open rectangular base for the placement of the base. The shell's primary purpose is to house the base unit which is securely placed into the bottom opening of the shell. Located on the top face of the shell are a plurality of openings that allow for the entry of the liquid into the interior of the shell where the base is located. The entry facilitates two features: the sinking of the device to the bottom of the container in which it is placed as the intake of the liquid through the openings located on the top of the shell increases the object's density, and therefore, forces the object to the bottom of the container; and the activation of the PCB by making contact with the exposed probes of the PCB.

The base, similar to the shell, is comprised of a transparent, food grade plastic. The base consists of three sections, the lower section, which is in the shape of a rectangle and contains a plurality of openings, an upper section which is a smaller rectangle with an opening for the placement of the PCB, and a cover which is hermetically sealed to the upper section and contains a plurality of openings that expose the conductive probes of the PCB. The openings contained on the lower section serve the same purpose as the openings located on the top of the shell, as previously described.

The PCB consists of a power source, an LED, two conductive probes, and one transistor. The PCB is assembled as such: the first probe is connected to the positive voltage of the power source, three (3) coin cell batteries producing a nominal supply of 4.5V; the second conductive probe is connected the transistor; and the transistor is of NPN variety, and placed between the LED's cathode and the circuit's ground.

When the device is placed in a liquid, the transistor has a positive voltage on the base which allows electrons to flow proportionally to the base voltage between the collector and emitter, closing the circuiting and illuminating the LED in a variety of colors. When the device is removed from the liquid, there is no positive voltage being applied to the base, and electrons are not allowed to flow between the collector and emitter, essentially opening the circuit and discontinuing the illumination of the LED.

D. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

We claim:

1. A liquid-activated light device, comprising:
   a. a hollow shell comprising one or more openings,
   b. a base comprising three sections: a lower section containing a plurality of openings, an upper section, and a base cover containing a plurality of holes; and
   c. a printed circuit board comprising: a power source, at least one LED located on either side of the PCB, a pair of conductive probes, and a transistor.

2. The device of claim 1, wherein the cover contains a plurality of holes equal in number to the conductive probes.

3. The device of claim 2, wherein the PCB is located in a cavity in the upper section of the base.

4. The device of claim 3, wherein the conductive probes of the PCB are exposed to the exterior of the base via the plurality of holes contained on the cover.

5. The device of claim 4, wherein the base is placed in an opening located on the shell of the device.

6. The device of claim 5, wherein the presence of a liquid, said liquid acts as a switch, closing the electrical circuit and illuminating the LED.

7. The device of claim 6, wherein the removal of the device from said liquid opens the circuit and the LED is no longer illuminated.

8. The device of claim 7, wherein immersed in a liquid, the plurality of holes located on the shell and lower section of the base allow the liquid to enter the interior of the shell of the device and facilitates sinking of the device to the bottom of the container.

9. A liquid activated lighted device, comprising:
   a. a hollow shell comprising one or more openings;
   b. a base comprising three sections: a lower section containing a plurality of openings, an upper section, and a base cover containing a plurality of holes; and
   c. a printed circuit board comprising: a power source, at least one LED located on either side of the PCB, a pair of conductive probes, and a transistor.

10. The device of claim 9, wherein the top contains a plurality of holes equal in number to the conductive probes.

11. The device of claim 10, wherein the PCB is located in a cavity in the upper section of the base.

12. The device of claim 11, wherein the conductive probes of the PCB are exposed to the exterior of the base via the plurality of holes contained on the cover.

13. The device of claim 12, wherein the base is located in the shell of the device.

14. The device of claim 13, wherein a soluble substance is located in the shell of the device.

15. The device of claim 14, wherein immersed in a liquid, the plurality of holes located on the shell and lower section of the base allow the device sinks to the bottom of the container.

16. The device of claim 15, wherein immersed in a liquid, the plurality of holes located on the shell and lower section of the base allow the soluble substance located within the shell to disperse throughout the liquid.

17. A liquid-activated light device, comprising:
   a. a hollow shell comprising one or more openings;
   b. a base comprising three sections: a lower section containing a plurality of openings, an upper section, and a base cover containing a plurality of holes; and
   c. a printed circuit board comprising: a power source, at least one LED located on either side of the PCB, a thermistor, and a transistor;
   wherein the cover contains a plurality of holes equal in number to the thermistor probes;
   wherein the PCB is located in a cavity in the upper section of the base;
   wherein the base is placed in an opening located on the shell of the device;
   wherein the presence of a liquid, said liquid acts as a switch, closing the electrical circuit and illuminating the LED;
   wherein the removal of the device from said liquid opens the circuit and the LED is no longer illuminated; and
   wherein immersed in a liquid, the plurality of holes located on the shell and lower section of the base allow the liquid to enter the interior of the shell of the device and allows device sinks to the bottom of the container.

* * * * *